United States Patent [19]
Conrad et al.

[11] Patent Number: 5,736,257
[45] Date of Patent: Apr. 7, 1998

[54] PHOTOACTIVATABLE POLYMERS FOR PRODUCING PATTERNED BIOMOLECULAR ASSEMBLIES

[76] Inventors: David W. Conrad, 8778 Old Colony Way, 2D, Alexandria, Va. 22309; Paul T. Charles, Jr., 8515 Grandhaven Ave., Upper Marlboro, Md. 20772

[21] Appl. No.: 428,454

[22] Filed: Apr. 25, 1995

[51] Int. Cl.$^6$ .............. B32B 27/08; G01N 33/53; C12M 1/00; C08F 2/46
[52] U.S. Cl. .............. 428/474.4; 522/2; 435/6; 435/7.1; 435/287.2
[58] Field of Search .............. 522/2; 428/474.4; 435/6, 7.1, 287.2

[56] References Cited

U.S. PATENT DOCUMENTS

| | | | |
|---|---|---|---|
| 4,103,064 | 7/1978 | McAlear et al. | 428/333 |
| 4,103,073 | 7/1978 | McAlear et al. | 428/474 |
| 4,562,157 | 12/1985 | Lowe et al. | 435/291 |
| 4,591,570 | 5/1986 | Chang | 436/518 |
| 4,722,906 | 2/1988 | Guire | 436/501 |
| 4,751,171 | 6/1988 | Ogawa | 430/299 |
| 4,979,959 | 12/1990 | Guire | 623/66 |
| 5,217,492 | 6/1993 | Guire | 623/11 |
| 5,258,041 | 11/1993 | Guire et al. | 623/66 |
| 5,316,784 | 5/1994 | Maurer et al. | 427/2 |

OTHER PUBLICATIONS

American Vacuum Society 41st National Symposium, Colorado Convention Center, Denver, Colorad, Oct. 24–28, 1991.

Vargo et al., "Adhesive Electroless Metallization of Fluoropolymeric Substrates", Science, vol. 262, Dec. 10, pp. 1711–1712, 1993.

Braybrook et al. "Organic Polymer Surfaces for use in Medicine: Their Formation, Modification, Characterisation and Application", Prog. Polym. Sci. vol. 15, pp. 715–734, 1990.

Wrotnowski, "Biochip Technology Offers Powerful Tools for Research and Diagnostics", Genetics and Engineering News, Nov. 15, 1994, p. 8.

Fodor et al. "Light–Directed, Spatially Addressable Parallel Chemical Synthesis", Research Article, Feb. 15, pp. 767–773, 1991.

Pritchard et al., "Micron–Scale Patterning of Biological Molecules", Angew. Chem. Int. Ed. Engl., 34, No. 1, pp. 91–93, 1995.

Prime et al., "Adsorption of Proteins onto Surfaces Containing End–Attached Oligo(ethylene oxide): A Model System Using Self–Assembled Monolayers", J. Am. Chem. Soc., 115, pp. 10714–10721, 1993.

Pale–Grosdemange et al., "Formation of Self–Assembled Monolayers by Chemisorption of Derivatives of Oligo(ethylene glycol) of Structure $HS(CH_2)_{11}(OCH_2CH_2)_mOH$ on Gold", J. Am. Chem. Soc., 113, pp. 12–20, 1991.

Lopez et al. "Scanning Electron Microscopy Can Form Images of Patterns in Self–Assembled Monolayers", Langmuir, vol. 9, pp. 1513–1516, 1993.

Parsons et al., "Multianalyte Assay System Developed for Drugs of Abuse", Clinical Chemistry, vol. 39, No. 9, pp. 1899–1903, 1993.

Kakabakos, et al. "Multianalyte Immunoassay Based on Spatially Distinct Fluorescent Areas Quantified by Laser–Excited Solid–Phase Time–Resolved Fluorometry", Clinical Chemistry, vol. 38, No. 3, pp. 338–342, 1992.

Ekins et al., "Development of Microspot Multi–Analyte Ratiometric Immunoassay Using Dual Fluorescent–Labelled Antibodies", Analytica Chemica Acta, 227, pp. 73–97, 1989.

(List continued on next page.)

*Primary Examiner*—Mark Chapman
*Attorney, Agent, or Firm*—Thomas E. McDonnell; John J. Karasek

[57] ABSTRACT

The presently claimed invention is directed to novel biochips and a method for forming said biochips and novel photoactivatable compounds, 2,6-DOCA, 2-NOCA and LC-ASA Amine.

7 Claims, 4 Drawing Sheets

OTHER PUBLICATIONS

Eggers et al., "A Microchip for Quantitative Detection of Molecules Utilizing Luminescent and Radioisotope Reporter Groups", BioFeature, vol. 17, No. 3, pp. 516–524, 1994.

Bhatia et al., "Fabrication of Surfaces Resistant to Protein Adsorption and Application to Two-Dimensional Protein Patterning", Analytical Biochemistry, 208, pp. 197–205, 1993.

Yan et al., "Photochemical Functionalization of Polymer Surface and the Production of Biomolecule-Carrying Micrometer-Scale Structures by Deep-UV Lithography Using 4-Substituted Perfluorophenyl Azides", J. Am. Chem. Soc. Vol. 115, No. 2, pp. 814–816, 1993.

Smithson et al., "Ultrathin Film Characterization: Photoreactive Polyacrylamide", Colloids Surfaces B: Biointerfaces, pp. 349–355, 1993.

Colby et al., "Light Activated Polymers for Flexible Surface Modification", Proceedings of the Medical Design & Manufacturing Conference, Jun. 3, 1992, New York, NY.

Amos et al., "Surface Modification of Polymers by Photochemical Immobilization", 17th Annual Meeting of the Society for Biomaterials, May 1–5, 1991, Scottsdale, Arizona.

FIG. 4(a)
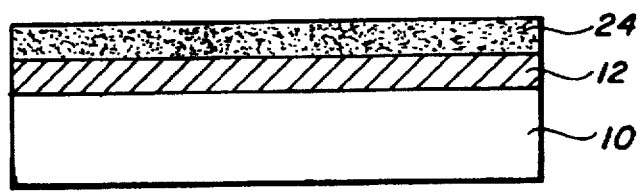
FIG. 4(b)
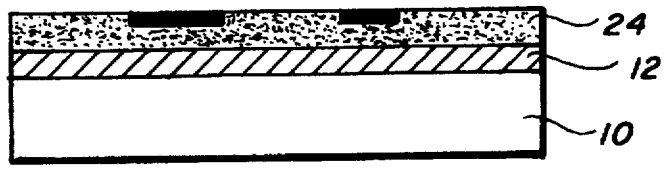
FIG. 4(c)
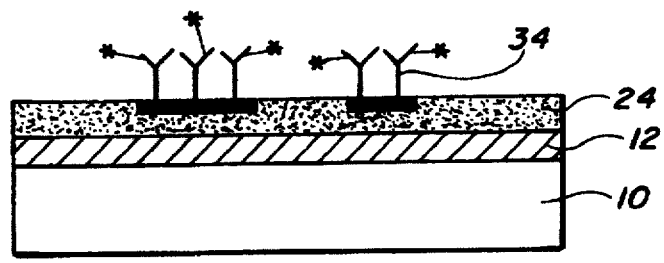

100 μm

PHOTOACTIVATABLE POLYMERS FOR PRODUCING PATTERNED BIOMOLECULAR ASSEMBLIES

BACKGROUND OF THE INVENTION

1. Field of the Invention

The presently claimed invention relates to photoactivatable polymers for producing patterned biomolecular assemblies. More particularly, the presently claimed invention relates to patterned network polymers formed upon substrates, the network polymers capable of binding biomolecules, and a method for forming the patterned network polymers upon various substrates for the subsequent binding of biomolecules such as antibodies or nucleic acid polymers.

2. Description of the Related Art

Most current immunoassay techniques allow for the quantitation of only one individual sample analyte per experiment. Although sequential detection strategies are possible, circumstances arise where the ability to detect multiple analytes simultaneously within a single sample is highly advantageous. For example, the analysis of soil samples from sites contaminated with a variety of toxic chemicals could be performed faster, cheaper, and with less test to test variability if the analyses for multiple analytes could be performed simultaneously rather than sequentially. Drug screening provides another area where one is usually interested in detecting more than one possible analyte. Finally, the clinical environment often requires the measurement of several related hormones to accurately diagnose and treat many endocrine disorders. The same can be said for other fields such as hematology, virology, and oncology.

The conventional approach to "multi-analyte" detection has generally relied on the use of multiple labels for key reagents in the immunoassay system to keep track of individual analytes. For example, dual assays have been developed in which one analyte was labeled with $^{125}I$ and the other with $^{131}I$. The two isotopes were later measured independently. Multiple fluorophores or enzyme labels have also been employed for a similar purpose. There are severe limitations imposed by the low number of useful radiolabels available for this application. Quantitation using multiple fluorophores is also difficult due to differences in photobleaching rates, limitations on the number of fluorescent dyes with appropriate excitation and emmision wavelengths, and fluorescence energy transfer. Using multiple enzymes as labels has the disadvantage of requiring multiple substrates and the correction for widely varying turnover rates. Even if these problems were overcome, the above methods would still be limited by the finite number of non-interfering different labels that could be employed in the same system on which multiple antibodies are immobilized. It is difficult to imagine a sensor of this type that could simultaneously detect hundreds of different analytes.

However, currently several broad strategies are being applied to the development of patterned surfaces on which multiple antibodies are immobilized. The first involves keeping the different antibodies physically separate throughout the immobilization procedure. The techniques employed range from simply applying the antibodies in individual stripes using a paintbrush, to microwriting, microstamping or microspotting. These methods are simple and flexible, but do not allow for the production of high resolution (submicron) protein patterns. The second strategy uses microlithography to produce active substrate regions formed by selective removal or photochemical conversion of reactive monolayers to produce discrete regions for antibody immobilization. See Amos, R. A. et al. Surface Modification of Polymers by Photochemical Immobilization-A General Method, The 17th Annual Meeting of the Society for Biomaterials, 1–5 May 1991, Scottsdale, Ariz., incorporated herein by reference in its entirety and for all purposes. See Clapper, D. L. et al., Covalent Immobilization of Cell Adhesion Proteins and Peptides to Promote Cell Attachment and Growth of Biomaterials, The 16th Annual Meeting of the Society for Biomaterials, 20–23 May 1990, Charleston, S.C., incorporated herein by reference in its entirety and for all purposes. See Colby, L. E. et al., Light Activated Polymers for Flexible Surface Modification, Proceedings of the Medical Design & Manufacturing Conference, Jun. 3, 1992, N.Y., N.Y., incorporated herein by reference in its entirety and for all purposes. See Smithson, R. L. W, et al., Ultrathin Film Characterization: Photoreactive Polyacrylamide, 1 Colloids and Surfaces B: Biointerfaces, pp. 349–355 (1993), incorporated herein by reference in its entirety and for all purposes. See Yah, M.; Cai, S. X.; Wybourne, M. N.; Keana, J. F. W. J. Am. Chem. Soc. 115, 814–816, 1993, incorporated herein by reference in its entirety and for all purposes. See also U.S. Pat. Nos. 4,722,906 (Guire); 5,258,041 (Guire); 5,217,492 (Guire); 4,979,959 (Guire), each patent incorporated herein by reference in its entirety and for all purposes. Modification of surfaces for increasd biocompatability as discussed by Amos, Clapper, Guire, Yah, Colby and Smithson, supra, differ from the present invention in that (a) they do not teach photoactivation prior to fabrication of arrays of biomolecules and (b) they do not teach that photoactivatable groups are a part of the structure of the formed photoactivatable polymers. See Bhatia, S. K.; Teixeira, J. L.; Anderson, M.; Shriver-Lake, L. C.; Calvert, J. M.; Georger, J. H.; Hickman, J. J.; Dulcey, C. S.; Schoen, P. E.; Ligler, F. S. Anal. Biochem. 208, 197–205, 1993, incorporated herein by reference in its entirety and for all purposes. See Eggers, M.; Hogan, M.; Reich, R. K.; Lamture, J.; Ehrlich, D.; Hollis, M.; Kosicki, B.; Powdrill, T.; Beattie, K.; Smith, S.; Varma, R.; Gangadharan, R.; Mallik, A.; Burke, B.; Wallace, D. BioTechniques, 17, 516–524, 1994, incorporated herein by reference in its entirety and for all purposes. See also U.S. Pat. Nos. 4,103,073 (McAlear et al.); 4,103,064 (McAlear et al.); 4,562,157 (Lowe et al.), each patent incorporated herein by reference in its entirety and for all purposes. See Ekins, R.; Chu, F.; Biggart, E. Analytica Chemica Acta., 227, 73–96, 1989, incorporated herein by reference in its entirety and for all purposes. Bhatia, Eggers, Lowe, McAlear and Elkins, supra, do not teach deposition and/or patterning of multiple (i.e. different) biomolecules. See also U.S. Pat. Nos. 4,591, 570 (Chang), incorporated herein by reference in its entirety and for all purposes. See Kakabakos, S. E.; Christopoulos, T. K.; Diamandis, E. P. Clin. Chem., 38, 338–342, 1992, incorporated herein by reference in its entirety and for all purposes. See Parsons, R. G.; Kowal, R.; LeBlond, D.; Yue, V. T.; Neargarder, L.; Bond, L.; Garcia, D.; Slater, D.; Rogers, P. Clin. Chem. 1993, 39, 1899–1903, incorporated herein by reference in its entirety and for all purposes. Chang, Kakabakos, and Parsons, supra, do not use photoactivation to determine the geometry of biomolecular arrays and do not describe a technique for the fabrication of micron scale biomolecular arrays. See Lopez, G. P.; Biebuyck, H. A.; Whitesides, G. M. Langmuir, 9, 1513–1516, 1993, incorporated herein by reference in its entirety and for all purposes. See Pale-Grosdemange, C.; Simon, E. S.; Prime, K. L.; Whitesides, G. M. J. Am. Chem. Soc., 113, 12–20, 1991, incorporated herein by reference in its entirety and for all purposes. See Prime, K. L.; Whitesides, G. M. J. Am. Chem. Soc. 115, 10714–10721, 1993, incorporated herein by reference in its entirety and for all purposes. Lopez, Pale-Grosdemange, and Prime, supra, only describe production of biomolecular arrays on gold surfaces via chemisorbed thiols. See Pritchard, D. J. et al., Micron-Scale Patterning of Biological Molecules, 34, No. 1, Angew. Chem. Int. Ed. Engl., pp. 91–93, 1995, incorporated herein by reference in its entirety and for all purposes. Pritchard, supra, describes deposition of two antibodies in distinct locations based on photoactivation of an aryl nitrene linked to biotin wherein the biotin moiety is bound to surface bound avidin. Pritchard has to add the aryl nitrene linked biotin (i.e. photoactivatable cross-linker) after deposition of the avidin on the surface of the substrate. In contrast, according to the presently claimed invention, the photoactivatable compound (e.g. 2,6-DOCA-which can be incorporated in any density or concentration desired) is an integral part of the polymer layer. Furthermore, according to the Pritchard technique, supra, the large size (360 Kd molecular weight) of the avidin limits the density of the aryl nitrene biotin bound to the substrate surface. See Fodor, S. P. A. et al., Light-Directed, Spatially Addressable Parallel Chemical Synthesis, Research Article, pp. 767–773, 15 Feb. 1991, incorporated herein by reference in its entirety and for all purposes. Fodor, supra, describes a method for the deposition of nucleic acid polymers or peptides upon a substrate, respectively. However, the deposition technique of Fodor, supra, requires that the deposition of the nucleic acid polymer or peptide be done one base pair or one amino acid at a time, respectively. See Smithson, R. L. W., et al., Ultrathin Film Characterization: Photoreactive Polyacrylamide, 1 Colloids and Surfaces B: Biointerfaces, pp. 349–355 (1993), incorporated herein by reference in its entirety and for all purposes. See also Wrotnowski, C., Biochip Technology Offers Powerful Tools for Reasearch and Diagnostics, Genetics and Engineering News, 15 November 1994 at page 8, incorporated herein by reference in its entirety and for all purposes. See also U.S. Pat. Nos. 4,591,570 (Chang); 4,751,171 (Ogawa); 4,103,073 (MeAlear et al.); 4,103,064 (MeAlear et al.); 4,562,157 (Lowe et al.); 4,722,906 (Guire); 5,258,041 (Guire); 5,217,492 (Guire); 4,979,959 (Guire), each patent incorporated herein by reference in its entirety and for all purposes.

One of the main problems encountered with most previously used methods for sequential protein immobilization in discrete locations has been the prevention of non-specific protein adsorption. This adsorption may occur at locations where a protein has been previously immobilized or at inactivated regions of a substrate surface. Extensive washing steps using salts and detergents have been required in attempts to partially alleviate these problems. See U.S. Pat. No. 4,562,157, supra, (Lowe et al.).

Although many organic polymers are known to be resistant to protein adsorption and possess good biocompatability, there are very few examples in the literature of the photochemical functionalization of polymer surfaces for biomolecule immobilization. See Braybrook, J. H.; Hall, L. D, Prog. Polym. Sci., 15, 715–734, 1990, incorporated herein by reference in its entirety and for all purposes. One involves the light-directed non-specific attachment of an N-hydroxysuccinimide perfluorophenyl azide to the surface of polystyrene. See Smithson, R. L. W., et al., Ultrathin Film Characterization: Photoreactive Polyacrylamide, 1 Colloids and Surfaces B: Biointerfaces, pp. 349–355 (1993), incorporated herein by reference in its entirety and for all purposes. See Yan, M.; Cai, S. X.; Wybourne, M. N.; Keana, J. F. W. J. Am. Chem. Soc. 115, 814–816, 1993, incorporated herein by reference in its entirety and for all purposes. This surface-bound heterobifunctional crosslinker is then allowed to react with protein amino groups to form covalent amide linkages. One disadvantage of this system is the multi-step procedure for polymer activation and subsequent protein immobilization.

SUMMARY OF THE INVENTION

It is therefore an object of the present invention to make a substrate having a pattern of one or more biomolecules.

It is another object of the present invention to make a polymer which can be readily activated to create a desired pattern for the subsequent attachment of one or more proteins to that pattern.

It is yet another object of the present invention to make a polymer which can be readily activated to create a desired pattern upon a substrate for the subsequent attachment of one or more antibodies upon that pattern.

It is still another object of the present invention to make a polymer which can be readily activated to create a desired pattern via a photochemical reaction upon a substrate for the subsequent attachment of biomolecules upon that pattern.

It is even another object of the present invention to make a polymer which can be readily activated to create a desired pattern via a photochemical reaction, the pattern having a resolution on the order of about 0.1 to about 100 microns, upon a substrate for the subsequent attachment of one or more biomolecules upon that pattern.

It is even yet another object of the present invention to make a polymer which can be readily activated to create a desired pattern via a photochemical reaction, the pattern having a resolution on the order of about 0.1 to about 100 microns, upon a substrate for the subsequent attachment of one or more proteins upon that pattern.

It is still yet another object of the present invention to make a polymer which can be readily activated to create a desired pattern via a photochemical reaction, the pattern having a resolution on the order of about 0.1 to about 100 microns, upon a substrate for the subsequent attachment of one or more antibodies upon that pattern.

It is even another object of the present invention to make a polymer which can be readily activated to create a desired pattern via a photochemical reaction, the pattern having a resolution on the order of 0.1 to 100 microns, upon a substrate for the subsequent attachment of two or more different biomolecules upon that pattern.

It is even yet another object of the present invention to make a polymer which can be readily activated to create a desired pattern via a photochemical reaction, the pattern having a resolution on the order of about 0.1 to about 100 microns, upon a substrate for the subsequent attachment of two or more different proteins upon that pattern.

It is still yet another object of the present invention to make a polymer which can be readily activated to create a desired pattern via a photochemical reaction, the pattern having a resolution on the order of about 0.1 to about 100 microns, upon a substrate for the subsequent attachment of two or more different antibodies upon that pattern.

It is a further object of the present invention to make a biochip wherein the biochip has attached upon its surface a pattern of two or more different biomolecules immobilized in different locations.

It is an even further object of the present invention to make a biochip wherein the biochip has attached upon its surface a pattern of two or more different proteins immobilized in different locations.

It is yet a further object of the present invention to make a biochip wherein the biochip has attached upon its surface a pattern of two or more different antibodies immobilized in different locations.

It is another object of the present invention to make a biochip wherein the biochip has attached upon its surface a patten of nucleic acid polymers such as DNA or RNA immobilized in different locations.

It is an object of the present invention to immobilize intact and fully functional biomolecules in patterned regions on the substrate surface.

It is still a further object of the present invention to make a biochip wherein the biochip has attached upon its surface a pattern of two or more different biomolecules immobilized in different locations, the pattern having a resolution on the order of about 0.1 to about 100 microns.

It is still an even further object of the present invention to make a biochip wherein the biochip has attached upon its surface of pattern of immobilized two or more different proteins, the pattern having a resolution on the order of about 0.1 to about 100 microns. It is yet an even further object of the present invention to make a biochip wherein the biochip has attached upon its surface of pattern of immobilized two or more different antibodies, the pattern having a resolution on the order of about 0.1 to about 100 microns.

These and other objects are accomplished by a process, the process comprising the steps of:

(1) providing a substrate having surface hydroxyls or capable of being modified to contain surface hydroxyl groups;

(2) modifying the substrate, if necessary, to contain surface hydroxyl groups;

(3) reacting the substrate surface hydroxyls with silanes to bind a molecular layer of vinyl groups upon the substrate;

(4) placing upon the molecular layer a solution of an acrylamide compound, a his-vinyl compound and a photoactivatable compound, each compound containing one or more vinyl groups which can participate in a free radical polymerization reaction to make a polymerized network layer bound to the molecular layer formed in step (3);

(5) photoactivating the polymerized network layer to make a patterned photoactivated polymerized network layer; and (6) placing upon the photoactivated polymerized network layer, one or more similar or dissimilar biomolecules to bind said biomolecules to said patterned photoactivated polymerized network layer.

In carrying out step (5), photoactivation of the polymerized network layer may be through an exemplary patterned mask having a desired resolution and shape, thereby, forming a patterned photoactivated polymerized network layer. Alternatively, a patterned photoactivated polymerized network layer may be formed without the use of a mask by using a directed laser beam forming a pattern of laser irradiated regions or by using a directed UV light source forming a pattern of UV irradiated regions, each method forming a patterned photoactivated polymerized network of desired resolution and shape.

Exemplary photoactivatable compounds containing a vinyl group capable of participating in free radical polymerization reactions and which can upon photoactivation bind to biomolecules may be selected from the group consisting of bis(((2,6-dinitrobenzyl)oxy)carbonyl)allyl amine (2,6-DOCA), bis(((2-nitrobenzyl)oxy)carbonyl)allyl amine (2-NOCA), LC-ASA allyl amine (LC-ASA Amine) or mixtures thereof.

BRIEF DESCRIPTION OF THE DRAWINGS

FIGS. 1(a), 2(a), 3(a), 4(a), 4(b) and 4(c) are sectional views showing the steps of a first embodiment for explanation of the method of this invention

DETAILED DESCRIPTION OF THE PREFERRED EMBODIMENTS

Figure 1A:
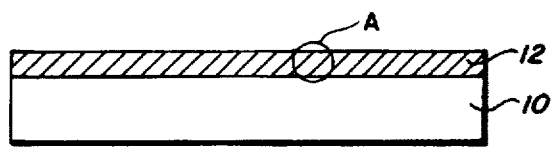

Detection of various analytes in a sample can be accomplished by the spatial isolation of a single detectable element on a solid support. According to this approach, the analyte present can be detected not by which label is attached to the analyte, but by where on the modified substrate (i.e. biochip) the label attached to the analyte is present. It is the prior knowledge of the type of biomolecule or bioactive agent immobilized on the discrete region of the substrate surface that allows for the identification and quantitation of multiple analytes.

In order to form the biochips wherein various biomolecules capable of binding to various analytes are immobilized upon modified substrates, the processes and compounds descried herein are used. While the following description of the compounds and processes used are described to aid in the understanding and use of the presently claimed invention, by no means is the following description meant to limit the scope of the presently described processes and compounds claimed.

Since it is recognized that various modified substrates are susceptible to the non-specific binding of biomolecules, it is necessary to control the degree of such non-specific adsorption of biomolecules in order to form blochips (e.g. substrates having modified surfaces with one or more biomolecules attached in discrete regions wherein the biomolecules may be the same or different). To this end, applicants have chosen surface chemistries that result in a substrate (or modified substrate) possessing inherent resistance to protein attachment (e.g. adsorption). The substrates can be further selectively modified to alter the inherent resistance to protein attachment (e.g. adsorption). After modification, substrate regions previously resistant to protein attachment (e.g. protein adsorption) now inherently promote protein attachment. In addition, the change in surface chemistry from inherent resistance to protein attachment to inherent susceptibility to protein attachment can be accomplished in a single step.

A suitable substrate is any material that contains surface hydroxyl groups or is capable of being modified to contain surface hydroxyl groups. For example, treatment of various substrates with $O_2$ plasma will provide a substrate with surface hydroxyl groups. Modification of substrates to provide surface hydroxyls are well known to those skilled in the art. Examples of substrates having surface hydroxyl groups or capable of being modified to contain surface hydroxyls include Si wafers, fused silica, silicate glasses, $SiO_2$, $Al_2O_3$, polyvinyl alcohol, indium tin oxide, tin oxide, zinc oxide, ceramics, fluoropolymers, diamond and others. See Vargo et al., Adhesive Electroless Metallization of Fluoropolymeric Substrates, Science, Vol. 262, pp. 1711–1712, (10 December 1993), incorporated herein by reference in its entirety and for all purposes. Substrates are treated with an exemplary silane of the formula:

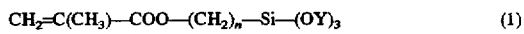  (1)

wherein n is an integer from 1–25, preferably from 1–5 and Y is either a halogen or a methyl or ethyl group. However, Y may be any leaving group wherein reaction between the exemplary silane (1) and substrate surface hydroxyl groups leads to the formation of an exemplary monomolecular film 12 of

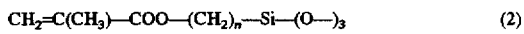  (2)

on first substrate 10. See FIGS. 1(a) and 1(b).

Another exemplary silane that may be used instead of silane (1) has the formula:

  (1a)

wherein x is an integer, preferably from 1–25 and Y is a halogen, a methyl group, an ethyl group, or any other suitable leaving group wherein reaction with surface hydroxyls of a substrate leads to the formation of an exemplary molecular layer having the formula:

  (2a)

In general, the molecules used for forming molecular films upon substrates having surface hydroxyl groups should have first reactive groups such as siloxy bonds that can react with the surface hydroxyl groups and also have second reactive groups such as terminal vinyl groups that can subsequently participate in polymerization reactions with, for example, acrylamide, bis-acrylamide and other vinyl group containing compounds to form network polymers thereof on the surface of the substrate.

An exemplary suitable silane for forming an exemplary monomolecular film 12 upon a first substrate 10 is the exemplary silane of the formula:

  (3)

Figure 1B:
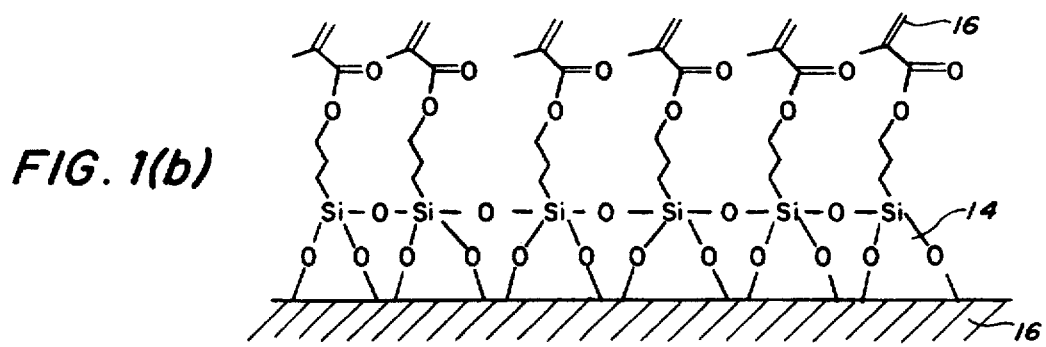
FIGS. 1(b), 2(b) and 3(b) are expanded views at the molecular scale level of the parts A, B, and C indicated in FIGS. 1(a), 2(a) and 3(a), respectively.

Exemplary silane (3) is also referred to by the abbreviation MPTS. The use of exemplary silane (3) upon a first substrate 10 having surface hydroxyls leads to the formation of an exemplary monomolecular film layer 12 as depicted in FIGS. 1(a) and 1(b). The monomolecular film 12 is hydrophilic in nature. The monomolecular film depicted in FIG. 1(b) has the general formula:

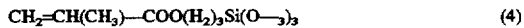  (4)

After having formed the monomolecular film 12 upon first substrate 10, the substrate and film can be immersed in an exemplary solution of acrylamide, a bis-acrylamide and photoactivatable compound containing a vinyl group (photoactivatable compound e.g. 2,6-DOCA; 2-NOCA; LC-ASA Amine, infra) which can participate in a free radical polymerization reaction. The immersion of the first substrate 10 coated with a hydrophilic molecular layer 12 in the acrylamide:bis-acrylamide:photoactivatable compound solution leads to the formation of a network polymer upon the hydrophilic layer 12 previously formed on first substrate 10. By varying the concentration of the photoactivatable compound (e.g. 2,6-DOCA) in the exemplary solution of acrylamide: bis acrylamide: photoactivatable compound solution, the final density of the photoactivatable groups within the resultant polymer can be readily controlled. The thickness of the network polymer formed is proportional to the amount of time the first substrate 10 with hydrophilic layer 12 is immersed in the exemplary solution of acrylamide:bisacrylamide:photoactivatable compound. The network polymer, alternatively, may also be formed upon layer 12 by spin coating or spraying the exemplary acrylamide:bis-acrylamide:photoactivatable compound solution on layer 12.

The bis-acrylamide acts as a cross-linker in the polymerization reaction leading to the formation of the network polymer. An exemplary molecular structure of the network polymer is shown in FIG. 3(b). While the exemplary structure shown in FIG. 3(b) is formed with the use of a cross-linker of the formula:

  (5)

wherein X=—CH$_2$, any bis-acrylamide type of molecule may be used having two terminal acrylamide moieties and wherein X=an alkyl linkage of varying chain length (e.g. —(CH$_2$)$_a$—), the length denoted by the integer a. Alternatively, a cross-linker of the formula:

  (5a)

or the formula:

  (5b)

may be used as the cross-linker wherein G is, for example, an alkyl group, a methylene group, an amide linkage or an alcohol linkage, among others and b is an integer from 1–10, preferably between 1–2 and R is an alkyl group of 1–5 carbon atoms. The critical feature of the cross-linker molecule is that it contains two terminal vinyl groups and is capable of forming a network polymer when reacted with a molecular film, acrylamide and a photoactivatable compound, each having terminal vinyl groups prior to the formation of the network polymer so formed.

A representative example of the formation of the network polymer upon an exemplary hydrophilic layer 12 upon first substrate 10 of FIGS. 1(a) and 1(b) using acrylamide, bis-acrylamide, and 2,6 DOCA is shown below:

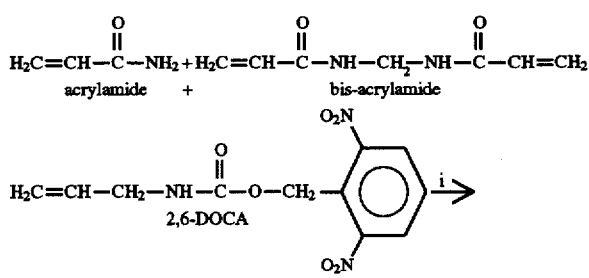

-continued

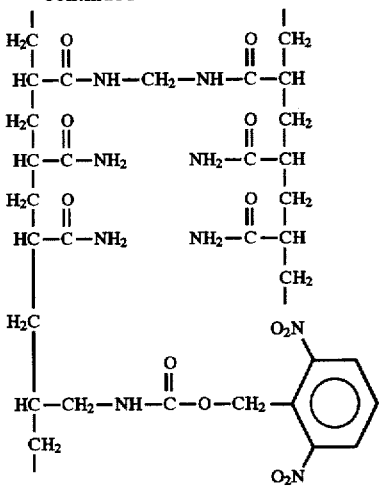

After formation of the polymer network of desired thickness, the first substrate 10 with molecular layer 12 coated with network polymer layer 24 (See FIG. 3(b)) is pulled out of the exemplary acryylamide:bis-acrylamide:2, 6-DOCA solution. As noted earlier, the network polymer layer 24 may, alternatively, be formed upon layer 12 by spin coating or spraying the exemplary acrylamide:bis-acrylamide:2,6-DOCA solution upon layer 12.

Figure 2A:
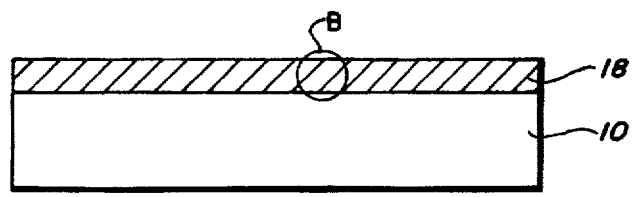
Figure 2B:
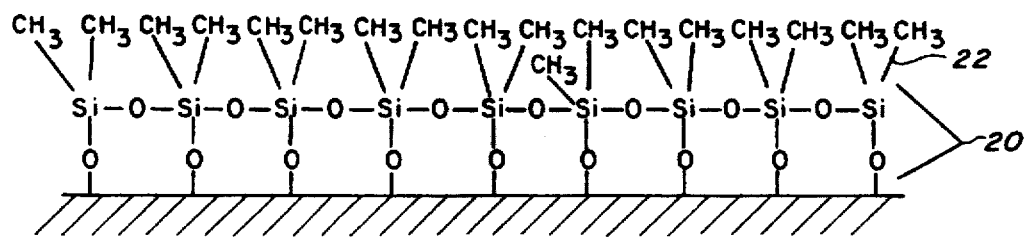

Alternatively, for the formation of thin layers 24 of the network polymer, a second substrate 10 having surface hydroxyls (See FIGS. 2(a) and 2b)) is reacted with a silane of the formula:

$$(CH_3)_2SiZ_2 \quad (7)$$

wherein Z is an ethoxy group, a methoxy group, a halogen or mixture thereof. An exemplary silane (7) is referred to by the abbreviation (DDMS) and has the formula:

$$(CH_3)_2SiCl_2. \quad (7a)$$

Reaction of second substrate 10 having surface hydroxyls with silane (7) or (7a) results in the formation of the following molecular film:

$$(CH_3)_2Si(O\text{---})_3 \quad (8)$$

upon the second substrate 10 denoted as film 18 in FIGS. 2(a) and 2(b). While the exemplary silane (7) is used, it is possible to use any silane wherein instead of two methyl groups, two alkyl groups are present on the silane (7). Thus, a silane of the formula:

$$(R)(R')SiZ_2 \quad (9)$$

may be used wherein R and R' are alkyl groups which may be the same or different and Z is any suitable leaving group such as a halogen, a methoxy group, an ethoxy group or mixtures thereof. The result of forming an exemplary molecular film 18 upon second substrate 10 (See FIGS. 2(a) and 2(b)) is that film 18 is hydrophobic as opposed to the exemplary hydrophilic film 12 formed on first substrate 10 as depicted in FIGS. 1(a) and 1(b).

Having formed a first substrate 10 having an exemplary hydrophilic molecular layer 12 and a second substrate 10 having an exemplary hydrophobic molecular layer 18, a sandwich of these two substrates is formed wherein layer 18 is placed adjacent to layer 12. Thereafter, the exemplary solution of acrylamide: bis-acrylamide: photoactivatable compound is placed between layers 18 and 12. Due to the hydrophilic nature and the availability of surface vinyl groups of layer 12 and the hydrophobic nature of layer 18 and the lack of vinyl groups (or other unsaturation capable of participating in the polymerization reaction, infra), a thin polymeric network layer 24 is formed upon layer 12 between layers 12 and 18. See FIGS. 3(a) and 3(b). The formation of the exemplary polymer network 24 has previously been described.

Figure 3A:
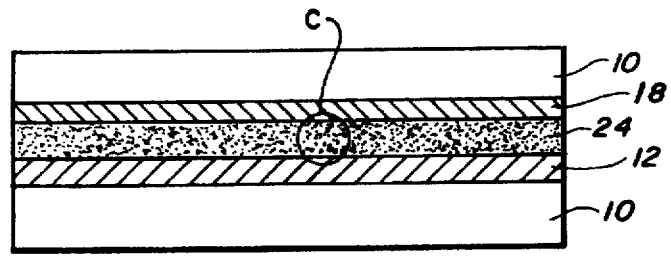
Figure 3B:
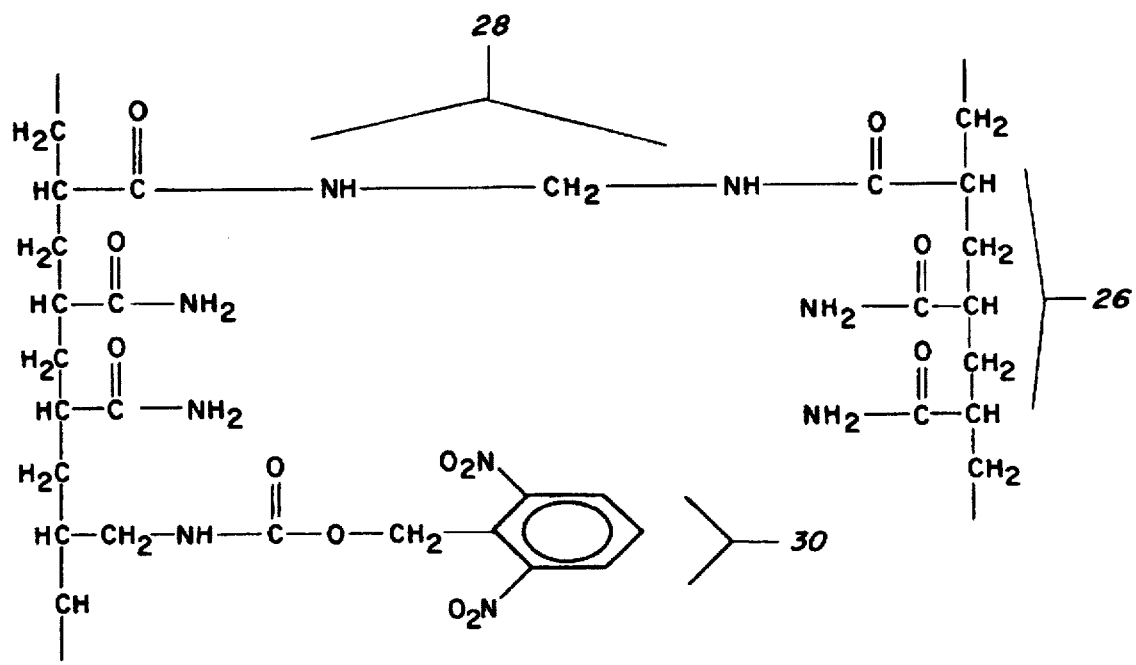

Due to the presence of the exemplary hydrophobic layer 18 which inhibits the growth of a thick layer 24 (shown in FIG. 3(a) and depicted at the molecular level in FIG. 3(b)), a very thin exemplary network polymer layer 24 is formed. Note that in FIG. 3(b), only one exemplary structure of the polymer network is shown. While any and all permutations possible in the bonding between the acrylamide, the exemplary bisacrylamide and the exemplary photoactivatable compound to form a polymer network 24 take place, not all permutations are depicted in FIG. 3(b). However, the formation of the various permutations are understood by those skilled in the art. Note that the vinyl groups of the acrylamide, the bis-acrylamide, the photoactivatable compound (e.g. 2,6-DOCA) and the layer 12 form the backbone of the polymer network upon first substrate 10, the exemplary backbone referred to by numeral 26 in FIG. 3(b). One can imagine a structure of the polymer network 24 as one that resembles a fish net attached to the first substrate 10 via the intervening exemplary molecular layer 12.

After formation of a thin polymer network layer 24, the second substrate 10 having layer 18 attached, is peeled away leaving behind a first substrate 10 having a molecular layer 12 interposed between the first substrate 10 and the polymer network layer 24. Note that the polymer network layer 24 has a dinitrobenzyl moiety 30 attached within the polymer network 24 as depicted in FIG. 3(b). At this stage, the polymer network layer 24 is inherently resistant to protein adsorption or other chemical protein attachment.

Exemplary subsequent irradiation of layer 24 in the deep-UV causes photodeprotection of the pendant carbamates (e.g. using 2,6-DOCA as the photoactivatable compound) to generate o-nitrosobenzaldehydes, carbon dioxide and free primary amines as depicted below:

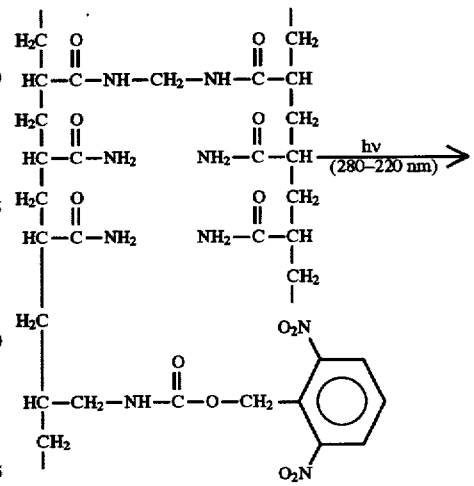

-continued

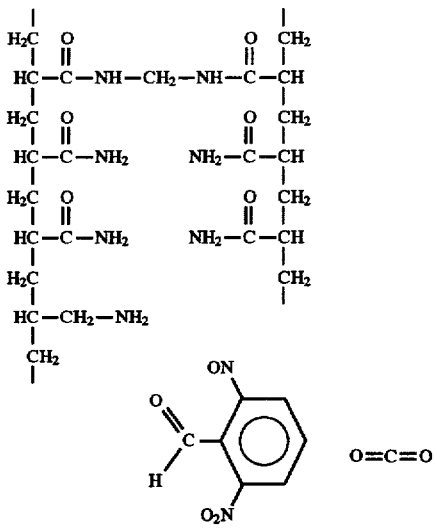

Note that irradiation may be done through a patterned mask, or by directed irradiation of laser light or UV light to specific portions of the polymer network 24 present upon the substrate 10.

The reactive exemplary aldehydes generated after irradiation are trapped within the exemplary polymer network 24 (polymer matrix) and can be reacted with primary amines on biomolecules to form imines (Schiff bases) as shown below:

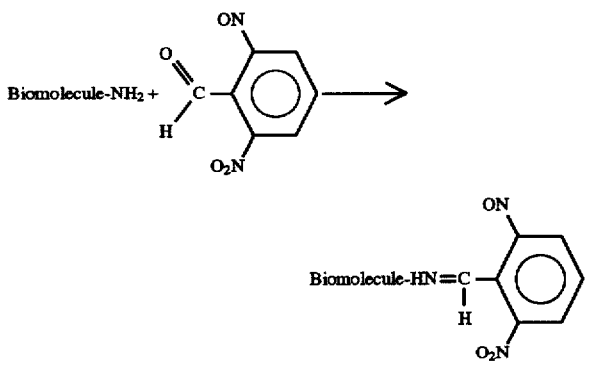

Thus, the light-driven generation of reactive aldehydes provides a method for the sequential immobilization of multiple biomolecules to the polymer surface in patterned arrays. Thus, a given region of the exemplary polymerized network layer 24 may be photoactivated followed by attachment of a particular biomolecule, such as the antibody IgG. Thereafter, another region of the same polymer network layer 24 (previously not photoactivated) may be photoactivated followed by attachment of a different biomolecule, such as the antibody IgM. In this fashion, of sequential photoactivation and attachment of biomolecules, biochips having two or more biomolecules can be attached to the underlying exemplary first substrate 10 in a pattern of desired shape and resolution. The resolution that can be achieved is between about 0.1 to about 100 microns, preferably between about 0.5 to about 50 microns, more preferably between about 0.75 to about 10 microns and most preferably from about 1 to about 5 microns.

Alternative, photoactivatable compounds that may be used in place of 2,6-DOCA are 2-NOCA and LC-ASA Amine, infra. LC-ASA Amine has the structure:

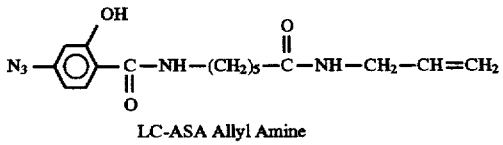
LC-ASA Allyl Amine

2-NOCA has the structure:

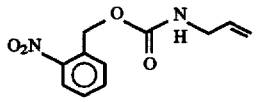

It should be noted that the method of altering a polymer's properties through incorporation of a photoactivatable compound with specific chemical properties is fully generalizable. Thus, the electrical, optical, and/or chemical properties of the polymer network formed could be readily varied by the choice of the photoactivatable compound used. In the choice of photoactivatable compound, the only requirement would be the presence of a vinyl group to participate in the free radical polymerization reaction and a photoactivatable group that can be irradiated with a light source to promote the binding of biomolecules to the photoactivatable group after irradiation. Thus, photoactivatable compounds such as LC-ASA Amine containing phenyl azides could be easily substituted for the 2,6-DOCA or 2-NOCA chemistry.

Alternatively, it is possible to attach highly-negatively charged biomolecules directly to the polymer network surface by forming ionic bonds between protonated amine groups on the polymer network and carboxylates and/or phosphates furnished by biomolecules.

Various kinds of biomolecules may be immobilized onto the patterns of the polymer network. For example, groups of antibodies exhibiting differential affinities to the same antigen could be used. The obvious advantage of operating the multi-analyte sensor in this configuration would be the availability of several independent signals to help confirm the presence of analytes of interest. In this manner, false-positive arising from cross-reactivity problems could be eliminated. Pattern recognition software could also benefit by differential-affinity antibodies. For example, image analysis programs could look for a specific pattern of exemplary fluorescence emanating from individual antibody groups before signaling the presence of an analyte.

It should be noted that while a HgXe lamp was used, photoactivation using an excimer laser (193 or 248 nm) is available as an alternative. Advantages associated with the use of the excimer laser include: 1) less light scattering and hence better resolution during irradiation, 2) the ability to work in projection mode, removing the need for a mask and minimizing cross-contamination and 3) greater flexibility in the types of patterns that can be formed by laser "writing" using a movable substrate stage.

The following examples are included to aid those skilled in the an to understand the operation of the presently claimed invention. The examples are merely exemplary and are not intended to limit the scope or breadth of the presently claimed invention.

EXAMPLES

Example 1: Synthesis of 2,6-DOCA-Derivatized Polyacrylamide and Immobilization of TRITC- and CY5-Labeled IgGs The first example of this invention is described in reference to FIGS. 1(a)–4(e). On a Si substrate (Si wafer, fused silica or glass) 10 there is formed by a chemical adsorption process, a monomolecular film 12 of:

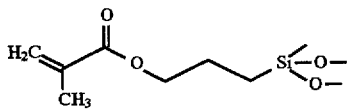

through the reaction of surface silanols and a reactive silane agent e.g. $H_2C=C(CH_3)CO_2(CH_2)_3Si(OCH_3)_3$ (MPTS). For example, the first group of substrates were immersed in a solution containing: methanol (193 mL), water (5.4 mL), glacial acetic acid (0.6 mL), and MPTS (1.0 mL) for 1 h at 60° C., to form a bonding 14 of:

at the $SiO_2$ surface FIG. 1(b). This chemisorption step leaves vinyl groups 16 at the substrate surface free to participate in the free radical polymerization reaction of acrylamide that covalently binds the polymer film to the substrate.

A second group of Si substrates were modified by a similar chemical adsorption process FIG. 2(a) to form a film 18 of:

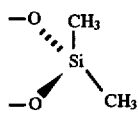

through the reaction with surface silanols and a reactive silane agent, e.g., $(CH_3)_2SiCl_2$ (dichlorodimethylsilane—DDMS). For example, the substrates were immersed for 1 h at room temperature in a solution of DDMS (1% v/v in hexane) to form a bonding 20 of:

In contrast to the earlier deposition of MPTS on the first substrate, this chemisorption step leaves methyl groups 22 at the second substrate surface which provides resistance to polymer attachment FIG. 2(b). When polymerization occurs between MPTS- and DDMS-modified substrates oriented in a "sandwich" configuration 24 as shown in FIG. 3(a), the polymer binds only to the MPTS-modified substrate. This allows the DDMS-modified substrate to be lifted off clean after polymerization.

The chemical components of the terpolymer used in this example are 1) acrylamide 2) bis-acrylamide and 3) 2,6-DOCA. The resulting polymer matrix, showing the poly-acrylamide backbone 26, bis crosslinks 28, and pendant 2,6-DOCA groups 30, is shown in FIG. 3(b). In a typical polymerization procedure, to 5.0 mL of water were added acrylamide (1.80 g) and bis-acrylamide (0.20 g) and the resulting solution was degassed for 10 min. To 1.0 mL of this stock solution was added 2,6-DOCA (3.0 mg). Potassium persulfate (2.0 mg) was added and the solution was sonicated, filtered through a 0.45 mm filter, and degassed for 5 min. To the solution was added N,N,N',N'-tetramethylethylenediamine (TEMED-3.0 μL). Within 1 min, 20 μL of the solution was applied to the surface of the MPTS-modified substrate, which was immediately covered with a DDMS-modified substrate. The resulting "sandwich" was pressed or clamped together with binder clips and allowed to polymerize for 12 h at room temperature. After lifting off the DDMS-modified substrate, the MPTS-modified substrate, containing the polymer film, was soaked in water for 15 min, sonicated for 10 s, and dried in a jet of $N_2$. Reproducible films with thicknesses of 1–2 μm as measured by a profilometer were produced using this technique.

Figure 5:
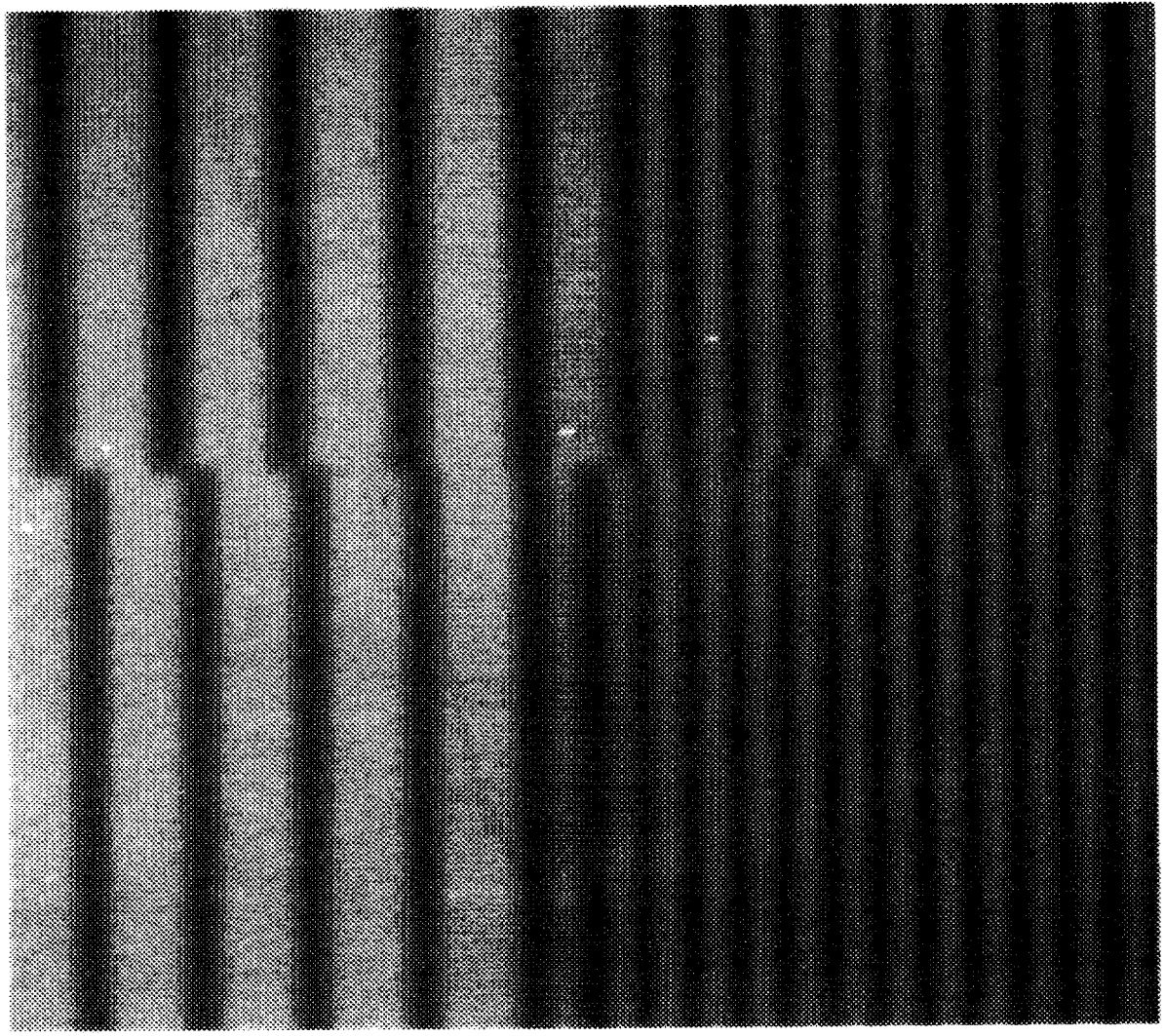
FIG. 5 is a Confocal Fluorescence Micrograph of TRITC-Labeled IgG biochip formed according to the presently claimed invention wherein the resolution of the pattern of antibodies is on the order of about 10 microns. The substrate upon which the pattern depicted in FIG. 5 is formed is fused silica ($SiO_2$).

In a typical procedure used for covalent attachment of antibodies to the activated region, the polymer-modified substrate FIG. 4(a–c) was irradiated through a mask 32 using a 500 W HgXe source (hv=260–220 nm, 11 mJ/cm²) were irradiated for 15 min. The substrate was rinsed with water and immersed in a solution of antibody (tetramethylrhodamine isothiocyanate (TRITC)-labeled goat IgG 34, 1 mg/mL in phosphate buffered saline (PBS)) for 30 min. It was rinsed and sonicated first in PBS and later in water. After drying in a jet of $N_2$, the substrate was visualized by confocal fluorescence microscopy. The resulting image (See FIG. 5) was produced using excitation of 514 nm and emission >565 nm. The dark areas correspond to regions blocked from deep-UV light by the metallized bars of the mask. Since photoactivation did not occur in the dark regions, there was little or no binding of fluorescently-labeled antibodies at these sites. The light areas correspond to irradiated regions and show increased fluorescence due to the attachment of TRITC-labeled antibodies.

Example 2: Synthesis of LC-ASA-Allyl Amine-Derivatized Polyacrylamide and Immobilization of HRP-Labeled Anti-Mouse IgGs The preparation of substrates was the same as in Example 1. The polymer was prepared in the dark as in Example 1 except that 3 mg of LC-ASA-Allyl Amine was substituted for 2,6-DOCA. Only 2 μL of TEMED were used for initiation. After polymerization and rinsing, 20 μL of a solution of HRP-labeled IgG (10 μg/mL in PBS) was applied to the polymer. A second fused silica slide was applied and the resulting "sandwich" was clamped together under a dark field mask with an open circle. Irradiation was carried out at 330 nm for 2 min. The slides were then separated, sonicated for 10 s. in PBS, and rinsed with copious amounts of water. To ascertain whether the labeled IgG had been bound in the irradiated region, a solution of the substrate for HRP (3,3', 5,5'-tetramethylbenzadine (TMB)) was layered over the slide. After 15 min. at room temperature the expected blue precipitate was clearly being formed only at the irradiated circle previously defined by the mask. This experiment demonstrated not only that the antibody had been selectively bound, but also that the HRP conjugate remained active after irradiation and immobilization.

Example 3: Sequential Immobilization of Anti-TRITC- and Anti-Fluorescein-IgGs on 2,6-DOCA-Derivatized Crosslinked Polyacrylamide Substrate preparation and film deposition were as in Example 1. Two identical polymer modified slides were irradiated using dark field slit (25 μm) masks. After rehydrating in water, they were then exposed to a solution of anti-fluorescein IgG (anti-FITC IgG) (0.1 mg/mL in PBS) for 1 h. They were then rinsed using a cycle of PBS, PBS-sodium dodecylsulfate (1% SDS), and finally with water. The masks were again placed over the slides, but this time the slits were rotated 90° to produce a cross relative to the previous irradiation region. The slides were irradiated for a second time. After rehydration, they were exposed to a solution anti-TRITC IgG (0.1 mg/mL in PBS) for 1 h. The substrate were taken through the same rinse cycle used earlier. One slide was exposed to a solution of FITC-labeled IgG (10 µg/mL in PBS) and the other slide was exposed to a solution of TRITC-labeled IgG (10 µg/mL in PBS). After 30 min., the slides were taken through the rinse cycle and dried in a jet of $N_2$. Both slides were imaged using the confocal microscope at both 488 and 514 nm. The slide exposed to FITC-labeled IgG showed only one bright stripe when scanned at both 488 nm (appropriate excitation line for FITC) and 514. The stripe was located in the region in which anti-FITC IgG was supposedly labeled. The results of the slide exposed to TRITC-labeled IgG were more ambiguous, however, since fluorescence was seen from both regions at both excitation wavelengths. This result might be due to a roughening of the polymer surface caused by irradiation which increases light scattering, or to a bleed over of fluorescence between channels of the confocal microscope. This type of crosstalk is always seen with fluorophores having broad emissions spectra when excited by closely spaced laser lines. This experiment demonstrates not only the possibility of sequential attachment, but it also illustrates that the immobilized antibodies are able to bind their respective antigens. Fluorescence from non-specific binding of fluorescently-labeled antibodies to unirradiated regions of the polymer was very low and was estimated to be less than 10% of that exhibited by antibodies bound in irradiated regions.

Example 4

Preparation of ((2-nitrobenzyl)oxy)carbonyl)allyl amine (2-NOCA) (1).

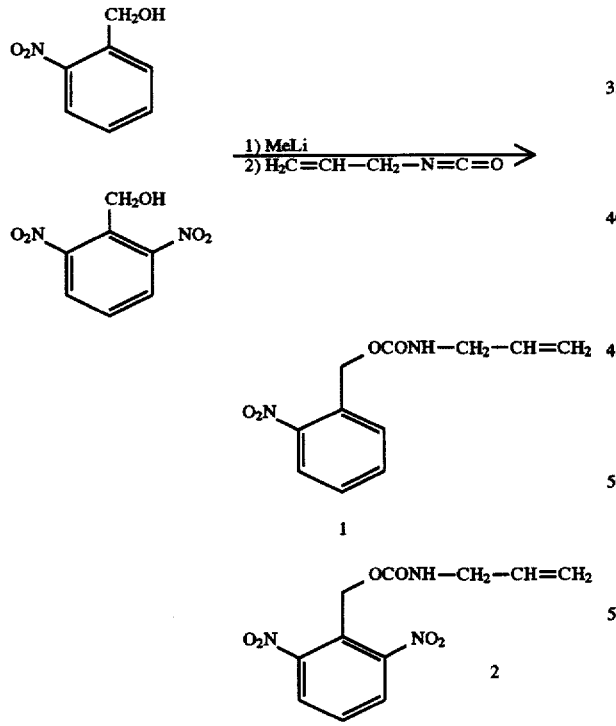

To a solution of 2-nitrobenzyl alcohol (Fluka) (7.0 g, 46 mmol) in anhydrous tetrahydrofuran (70 mL) at room temperature under argon was added an ethereal solution of methyllithium (1.42 M, 3.25 mL, 4.60 mmol). The resulting solution was stirred under these conditions for 2 h and then treated dropwise with a solution of allyl isocyanate (Aldrich) (4.1 mL, 3.9 g, 46 mmol) in dry tetrahydrofuran (45 mL).

Once the addition was complete, the solution was stirred for 30 min and concentrated in vacuo. The residue was taken up in ether (300 mL) and washed with water (3×200 mL) and brine (1×200 mL). After drying ($MgSO_4$), the solvent was removed under reduced pressure to give a crude light yellow solid (9.24 g). The pure product was isolated by extraction with hot hexane (3×50 mL). After cooling to 4° C. for 12 h, the desired carbamate 1 crystallized as long white needles (7.56 g, 70%) mp 59°–61 ° C. Anal. Calcd for $C_{11}H_{12}N_2O_4$ (236.23): C, 55.93; H, 5.12; N, 11.86. Found: C, 55.84; H, 5.01; N, 11.73. IR ($cm^{-1}$, KBr): 3314 (s, N-H str), 1697 (s, C=O str), 1521 (s, asymm N-O str), 1341 (m, symm N-O str). $^1H$ NMR (ppm, $CDCl_3$): d 3.83 (2 H, t, $RCHCH_2NHR$), 4.85–5.10 (1 H, br s, $^-NH^-$), 5.13–5.25 (2 H, complex m, $CH_2=CHR$) 5.53 (2 H, s, $CH_2OCOR$), 5.78–5.93 (1 H, complex m, $CH_2=CHR$) 7.47 (1 H, dt ($J_o$=8 Hz, $J_m$=2 Hz), H para to $NO_2$), 7.62 (2 H, overlapping dd, 2H, meta to $NO_2$), 8.09 (1 H, d ($J_o$=8 Hz), H ortho to $NO_2$). $^{13}C$ NMR: d 43.46 ($RCHCH_2NHR$), 63.23 ($H_2COCOR$), 116.20 ($CH_2$=CHR), 124.87(C ortho to $NO_2$), 128.47 (C ortho to $CH_2OCOR$), 128.64 (C para to $CH_2OCOR$), 133.09 (C para to $NO_2$), 133.68 ($CH_2$=CHR), 147.27 (C ipso to $NO_2$), 155.62 ($CH_2OCOR$).

Example 5

Preparation of ((2,6-dinitrobenzyl)oxy)carbonyl) allyl amine (2,6-DOCA) (2).

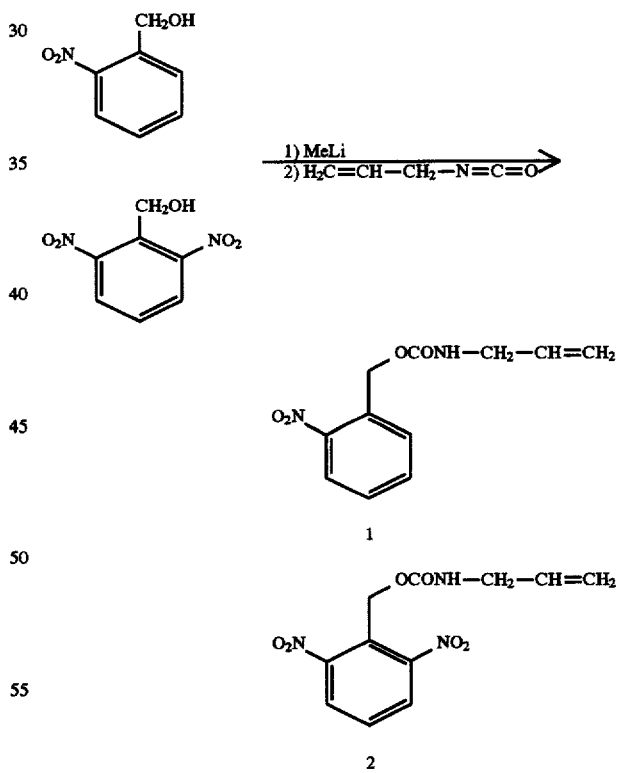

To a solution of 2,6-dinitrobenzenemethanoi (2.01 g, 10.1 mmol—See Houlihan, F. M.; Shugard, A.; Gooden, R.; Reichmanis, E. Macromolecules 21, 2001, 1988, incorporated herein by reference in its entirety and for all purposes) in anhydrous tetrahydrofuran (15 mL) at room temperature under argon was added an ethereal solution of methyllithium (1.42 M, 0.72 mL, 1.02 mmol). The resulting solution was stirred under these conditions for 2.5 h and then treated dropwise with a solution of allyl isocyanate (Aldrich) (0.90 mL, 0.85 g, 10.2 mmol) in dry tetrahydrofuran (10 mL).

Once the addition was complete, the solution was stirred for 30 min and concentrated in vacuo. The residue was taken up in ether (150 mL) and washed with water (3×25 mL) and brine (1×25 mL). After drying (MgSO$_4$), the solvent was removed under reduced pressure to give a brown solid (2.86 g), which after flash chromatography on silica gel (dichloromethane) afforded the desired carbamate 2 as a light yellow solid (1.76 g, 62%), mp 99°–100° C. Anal. Calcd for $C_{11}H_{11}N_3O_6$ (281.06): C, 46.96; H, 3.94; N, 14.95. Found: C, 46.91; H, 3.55; N, 14.91. IR (cm$^{-1}$, KBr): 3409 (s, N-H str), 1719 (s, C=O str), 1530 (s, asymm N-O str), 1368 (m, symm N-O str). $^1$H NMR (ppm, CDCl$_3$): d 3.72 (2 H, t, RCHCH$_2$; NHR), 4.77–4.90 (1 H, br s, ⁻NH⁻), 5.05–5.20 (2 H, complex m, CH$_2$=CHR), 5.53 (2 H, s, CH$_2$OCOR), 5.65–5.85 (1 H, complex m, CH$_2$=CHR) 7.65 (1 H, t (J$_o$=8 Hz), H meta to NO$_2$), 8.01 (2 H, d (J$_o$=8 Hz), H ortho to NO$_2$). $^{13}$C NMR: d 43.32 (RCHCH$_2$NHR), 58.37 (H$_2$COCOR), 116.18 (CH$_2$=CHR), 126.70 (C ipso to CH$_2$OCOR), 127.67 (C para to CH$_2$OCOR), 129.77 (C meta to CH$_2$OCOR), 133.75 (CH$_2$=CHR), 150.77 (C ipso to NO$_2$), 154.90 (CH$_2$OCOR).

Example 6
Preparation of LC-ASA-Allyl Amine (LC-ASA Amine).

CH$_2$=CH—CH$_2$—NH$_2$  +

Allyl Amine

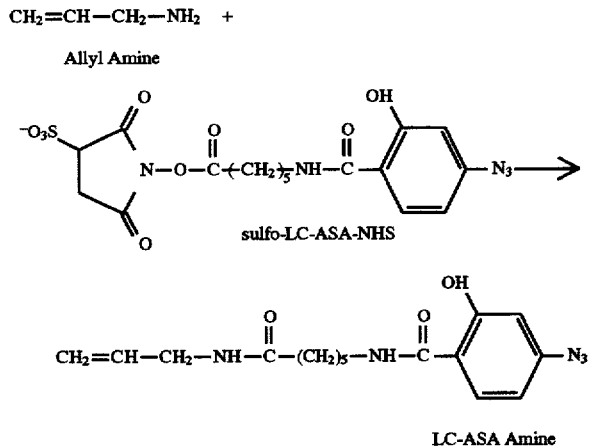

sulfo-LC-ASA-NHS

LC-ASA Amine

To 1.0 mL of sodium borate buffer (100 mM, pH 8.5) was added 10 mL allyl amine (Aldrich). The resulting solution was added to 50 mg sulfo-NHS-LC-ASA (Pierce Chemical Co.). The reaction mixture was stirred for 1 h. in the dark. The precipitate which formed was filtered and washed with water (25 mg, 75%). $^1$H NMR (ppm, CDCl$_3$): d 7.4 (d, 1H arom.), 7.3 (s, 1H arom.), 6.8 (broad s, 1H OH), 6.5 (d, 1H arom.), 5.9–5.7 (m, 1H CH$_2$=CH), 5.6 (broad s, 1H NH), 5.2 (d, 2H CH$_2$=CH), 3.8 (t, 2H CH$_2$—NHCO), 3.4 (q, 2H CH$_2$—NH), 2.2 (t 1H NHCO), 1.8–1.6 (m 6H methylene groups), 1.4–1.3 (m 2H methylene group).

We claim:

1. A biochip for detecting multiple analytes, said biochip comprising:

a substrate coated with two or more biomolecules in a pattern wherein said biomolecules are attached to said substrate via an intervening polymerized network layer, said polymerized network layer formed by the polymerization and photoactivation of acrylamide, a bis vinyl compound, and a photoactivatable compound, each of said acrylamide and said compounds containing one or more vinyl groups.

2. The biochip of claim 1 wherein said bis-vinyl compound has the structure:

(G)$_b$—(CR=CH$_2$)$_2$ wherein G is selected from the group consisting of an alkyl linkage, an amide linkage, an alcohol linkage or mixtures thereof and b is an integer from 1–10 and R is either hydrogen or an alkyl group of 1 to 5 carbon atoms.

3. The biochip of claim 1 wherein said bis-vinyl compound is bis-acrylamide.

4. The biochip of claim 1 wherein said photoactivatable compound is selected from the group consisting of 2,6-DOCA, 2-NOCA, LC-ASA Amine or mixtures thereof.

5. The biochip of claim 1 wherein said biomolecule is a protein.

6. The biochip of claim 1 wherein said biomolecule is an antibody.

7. The biochip of claim 1 wherein said biomolecule is a nucleic acid polymer.

* * * * *